(12) United States Patent
Marashdeh et al.

(10) Patent No.: US 10,269,171 B2
(45) Date of Patent: Apr. 23, 2019

(54) INTERACTIVE AND ADAPTIVE DATA ACQUISITION SYSTEM FOR USE WITH ELECTRICAL CAPACITANCE VOLUME TOMOGRAPHY

(71) Applicant: Tech4Imaging LLC, Columbus, OH (US)

(72) Inventors: Qussai Marashdeh, Columbus, OH (US); Geoffrey Legg, Tewksbury, MA (US); David Matthews, Concord, MA (US); Mohd Harish, Columbus, OH (US)

(73) Assignee: Tech4Imaging LLC, Columbus, OH (US)

( * ) Notice: Subject to any disclaimer, the term of this patent is extended or adjusted under 35 U.S.C. 154(b) by 863 days.

(21) Appl. No.: 14/191,574

(22) Filed: Feb. 27, 2014

(65) Prior Publication Data

US 2014/0365152 A1 Dec. 11, 2014

Related U.S. Application Data

(60) Provisional application No. 61/828,945, filed on May 30, 2013.

(51) Int. Cl.
*G01R 25/00* (2006.01)
*G01R 27/00* (2006.01)
(Continued)

(52) U.S. Cl.
CPC ............ *G06T 15/08* (2013.01); *G01F 1/64* (2013.01); *G01F 1/7046* (2013.01); *G01N 27/24* (2013.01);
(Continued)

(58) Field of Classification Search
CPC ................................................... G01T 15/08
See application file for complete search history.

(56) References Cited

U.S. PATENT DOCUMENTS 5,130,661 A 7/1992 Beck et al.
5,262,730 A 11/1993 Smith et al.
(Continued)

FOREIGN PATENT DOCUMENTS

CN 102954854 A 3/2013
EP 0606115 A1 * 7/1994 ........... G01D 5/2417
(Continued)

OTHER PUBLICATIONS

Huang et al; "Design of sensor electronics for electrical capacitance tomography"; IEE Proceedings-G, vol. 139, No. 1, Feb. 1992.*
(Continued)

*Primary Examiner* — Mohamed Charioui
*Assistant Examiner* — Leonard S Liang
(74) *Attorney, Agent, or Firm* — Standley Law Group LLP

(57) ABSTRACT

A control system and data acquisition system for an electrical capacitance tomography sensor comprised of a sensor having a plurality of electrodes, where each electrode is further comprised of a plurality of capacitance segments. Each of the capacitance segments of each electrode can be individually addressed to focus the electric field intensity or sensitivity to desired regions of the electrodes and the sensor.

21 Claims, 11 Drawing Sheets

(51) Int. Cl.
*G01D 18/00* (2006.01)
*G01D 21/00* (2006.01)
*G01P 21/00* (2006.01)
*G06T 15/08* (2011.01)
*G01N 27/24* (2006.01)
*G01F 1/64* (2006.01)
*G01F 1/704* (2006.01)
*G01N 21/27* (2006.01)
*G01R 35/00* (2006.01)
*G06F 17/50* (2006.01)
*G01R 27/02* (2006.01)
*A61B 5/05* (2006.01)

(52) U.S. Cl.
CPC ......... *A61B 5/05* (2013.01); *A61B 2562/0214* (2013.01); *G01N 21/274* (2013.01); *G01R 27/02* (2013.01); *G01R 35/005* (2013.01); *G06F 17/5036* (2013.01); *G06T 2211/428* (2013.01)

(56) References Cited

U.S. PATENT DOCUMENTS

| | | | |
|---|---|---|---|
| 6,208,204 B1* | 3/2001 | Suzuki | H03F 1/3229 330/149 |
| 7,424,462 B2* | 9/2008 | Avni | B82Y 10/00 382/156 |
| 7,684,846 B2 | 3/2010 | Johnson et al. | |
| 8,519,722 B1* | 8/2013 | Prendergast | G06F 3/044 324/658 |
| 8,614,707 B2* | 12/2013 | Warsito | A61B 5/0535 345/419 |
| 8,867,928 B2* | 10/2014 | Piehler | H04B 10/25751 398/193 |
| 9,016,143 B2* | 4/2015 | Mamigonians | G01L 1/142 324/649 |
| 9,170,224 B2 | 10/2015 | Fan et al. | |
| 9,581,560 B2 | 2/2017 | Fan et al. | |
| 2002/0028010 A1* | 3/2002 | Toida | G06T 7/0012 382/131 |
| 2003/0020493 A1* | 1/2003 | Haase | G01F 1/64 324/664 |
| 2003/0173958 A1 | 9/2003 | Goldfine et al. | |
| 2004/0233191 A1 | 11/2004 | Mukherjee | |
| 2005/0167588 A1* | 8/2005 | Donnangelo | A61B 5/0536 250/307 |
| 2007/0024278 A1 | 2/2007 | Walters et al. | |
| 2007/0133746 A1* | 6/2007 | Ortiz Aleman | G01F 1/64 378/59 |
| 2008/0116995 A1* | 5/2008 | Kim | H01P 1/181 333/161 |
| 2009/0272028 A1 | 11/2009 | Drozd et al. | |
| 2010/0097374 A1* | 4/2010 | Fan | A61B 5/0535 345/420 |
| 2010/0132473 A1 | 6/2010 | Willcox | |
| 2010/0148804 A1 | 6/2010 | Jakoby et al. | |
| 2010/0332170 A1 | 12/2010 | Gao et al. | |
| 2011/0109911 A1* | 5/2011 | Podoleanu | A61B 3/102 356/451 |
| 2012/0038368 A1 | 2/2012 | Mahalingam et al. | |
| 2012/0268135 A1 | 10/2012 | Marsala et al. | |
| 2013/0085365 A1* | 4/2013 | Marashdeh | A61B 5/05 600/386 |
| 2013/0187641 A1 | 7/2013 | Singer | |
| 2013/0275082 A1 | 10/2013 | Follmer | |
| 2014/0361793 A1* | 12/2014 | Marashdeh | G01N 27/24 324/663 |
| 2015/0338364 A1 | 11/2015 | Fan et al. | |
| 2016/0091448 A1 | 3/2016 | Soleimani | |
| 2016/0206227 A1 | 7/2016 | Marashdeh et al. | |

FOREIGN PATENT DOCUMENTS

| | | | |
|---|---|---|---|
| WO | WO 2009030876 A1 * | 3/2009 | G01N 27/22 |
| WO | WO 2010007096 A3 * | 3/2010 | G01F 1/56 |
| WO | WO 2011002793 A1 * | 1/2011 | G01N 27/228 |
| WO | WO 2011113169 A1 * | 9/2011 | A61B 5/0536 |

OTHER PUBLICATIONS

Wang et al, "Electrical Capacitance Volume Tomography: Design and Applications"; Sensors 2010, 10, 1890-1917.*
Warsito et al, Electrical Capacitance Volume Tomography; IEEE Sensors Journal, vol. 7, No. 4, Apr. 2007.*
Wikipedia entry for Electrical capacitance volume tomography.*
Huang et al., Design of Sensor Electronics for Electrical Capacitance Tomography, IEE Proceedings G (Circuits, Devices and Systems), vol. 139, Issue 1, Feb. 1992, p. 83-88.
Chew, W. et al., Reconstruction of Two-Dimensional Permittivity Distribution Using the Distorted Born Iterative Method, IEEE Transactions on Medical Imaging, Jun. 1990, pp. 218-225, vol. 9, No. 2.
Marashdeh, Q. et al., Adaptive Electrical Capacitance Volume Tomography, IEEE Sensors Journal, Apr. 2014, pp. 1253-1259, vol. 14, No. 4.
Xie, C. et al., Electrical Capacitance Tomography for Flow Imaging: System Model for Development of Image Reconstruction Algorithms and Design of Primary Sensors, IEEE Proceedings-G, Feb. 1992, pp. 89-98, vol. 139, No. 1.
Yang, W. et al., Image Reconstruction Algorithms for Electrical Capacitance Tomography, Measurement Science and Technology 14, 2003, pp. R1-R13.
Marashdeh, et al., "On the ECT Sensor Based Dual Imaging Modality System for Electrical Permittivity and Conductivity Measurements", 2006, pp. 1-6, The Ohio State University, Columbus, Ohio.
Warsito, et al., "Electrical Capacitance Volume Tomography", 2007, pp. 1-9.
Covilakam, M., "Evaluation of Structural Monitoring Methods for Large Diameter Water Transmission Pipelines", Dec. 2011, The University of Texas at Arlington.

* cited by examiner

Fig. 1: CT Scanned ECVT

Ping pong balls in a bed of 185um glass beads.

INTERACTIVE AND ADAPTIVE DATA ACQUISITION SYSTEM FOR USE WITH ELECTRICAL CAPACITANCE VOLUME TOMOGRAPHY

CROSS-REFERENCE TO RELATED APPLICATIONS

This application claims priority to [provisional/co-pending] U.S. Application No. 61/828,945 filed on May 30, 2013 and is herein incorporated by reference in its entirety.

BACKGROUND OF THE INVENTIVE FIELD

Electrical Capacitance Tomography (ECT) is the reconstruction of material concentrations of dielectric physical properties in the imaging domain by inversion of capacitance data from a capacitance sensor. Volume capacitance imaging or ECVT is the direct 3D reconstruction of volume concentration or physical properties in the imaging domain utilizing 3D features in the ECVT sensor design.

Dynamic ECVT is a technology that senses measured capacitances between a sensor plates to generate a whole volume image of the region. ECVT technology has been applied in providing images of objects moving through a pipe for example. ECVT has provided insights into multiphase flow phenomena in many industrial processes often in a combination of gas, liquid, and solid states, including pneumatic conveying, oil pipe lines, fluidized beds, bubble columns and many other chemical and biochemical processes. It may also be used for imaging biological processes and tissues.

Adaptive ECVT is an advanced technology that introduces a new dimension into 3D sensor design by applying voltages of different frequencies, amplitudes, and phases to capacitance plate segments. Adaptive sensors can provide a virtually infinite number of independent capacitance measurements of the flow field or imaging volume through which high resolution images can be obtained.

Data acquisition systems have been developed to sense capacitance measurements of capacitance sensors while rejecting parasitic capacitances inherit in ECT or ECVT sensors. Systems developed thus far are not flexible enough to cope with modern applications of capacitance tomography sensors.

The present invention relates to a data acquisition system that can increase imaging resolution through sensing capacitances from 3D conventional and adaptive capacitance sensors. In the preferred embodiment, interactive control of the data acquisition system allows for the zooming and focusing of the imaging resolution toward a region in the imaging domain (e.g., one of the voids). This is achieved through a unique design and set of features explained below.

SUMMARY OF THE GENERAL INVENTIVE CONCEPT

The present invention is directed to process tomography and, in particular, to an electrical capacitance volume tomography (ECVT) system using an adaptive and interactive data acquisition system that allows for the addressing of different segments of an adaptive capacitance sensor for steering the electric field direction toward the region of interest, focusing of the imaging region, increasing of volume image resolution, and allowing interactive control of acquisition parameters for self calibration and smart adjustments of an ECVT or AECVT (Adaptive Electrical Capacitance Volume Tomography) sensor.

Data acquisition systems were previously developed to measure capacitance between plates of a capacitance sensor based on charge/discharge method. An alternative AC based technique for measuring capacitances in a tomography sensor was also previously introduced. A field programmable gate array (FPGA) for controlling an AC based measuring circuitry was also used. The design of the present invention utilizes an FPGA for advanced control of the measuring circuit.

The present invention provides an innovative design with features through which the data acquisition system can respond intelligently and interactively to address different flow conditions. Specifically, features include a self calibration capacitor that acts as a reference for calculating capacitance and for allowing for self adjustments, and temperature sensing based on an embedded capacitor in the sensor wall. The present invention also provides the ability for:

i.) automatic control of the system by changing a balance signal through an attenuator,
ii.) real-time reconstruction by embedding a reconstruction algorithm in FPGA;
iii.) real-time auto-correction;
iv.) back calculation of a capacitance by using a reference capacitor,
v.) adaptive measurement of capacitance in an adaptive sensor by applying different attenuations to different excitation segments, and
vi.) detection of active electric signal parameters in the imaging domain. Details of these features are described below.

The interactive design of the present invention also preferably includes a temperature sensing mechanism for applications that involve wide variations in flow temperature. A temperature sensor is established by embedding capacitance plates, which are electrically isolated, in the capacitance sensor wall. A relation is established by measuring temperature variation and capacitance measurement of the embedded sensor. Recorded data is then used as a lookup table to read the temperature of the sensor wall for flows with high or varying temperatures. Similar mechanisms can be applied to measure capacitance change in different plate combinations in an empty sensor. These readings enable isolation of capacitance change due to changes in the sensor plate and sensor wall, and those related to change of temperature in the flow itself. Prior art related to capacitance devices for temperature measuring involve specific materials and manufacturing processes through which capacitance of parallel or symmetric plate capacitors relates predicatively to temperature change. In the present invention however, capacitance plates of various shapes and sizes are used to relate changes in plates and sensor wall temperatures to flow temperatures.

The interactive design of the present invention includes online updating of balance signals to account for accumulation and physical changes in the capacitance sensor. Such changes include corrosion of the internal wall of the sensor or the accumulation of solids. Preferably, a reference capacitor is used to compare changes between the sensor model/design to measured values. A balance signal is adjusted accordingly to recalibrate the capacitance sensor automatically. The balance signal can also be used to focus on a specific range of capacitance change selected by user. In other words, measured capacitance has a minimum and maximum value determined by calibration and based on material properties expected to be present in the imaging domain. When actual capacitance variation is in a range smaller or larger than calibration limits, the balance signal can be adjusted to compensate for this discrepancy and thus ensuring that the system measuring resolution covers the dynamic range of the capacitance being measured. This adjustment may also involve adjusting the programmable gain amplifier (PGA) to utilize maximum possible dynamic range of electronics.

The interactive design of the present invention also preferably involves setting values for attenuators, balance gains, and a PGA based on Bayesian prediction for real-time adjustments of sensor and calibration parameters. Bayesian prediction uses new measurements to update its estimation of parameters in real-time. This enables the system to adapt to new pattern in the flow as they develop over time.

The interactive design of the present invention also preferably involves embedding a reconstruction algorithm in the FPGA for real-time imaging. It also preferably involves storing parameters for test objects relative to the reference capacitor. Interactive features allow resurrection of static test objects by applying their parameters of capacitance data and comparing reconstructed images to stored shapes. Such features enable the data acquisition system to test the integrity of measurements online and compensate for changes in system components by adjusting the image to match stored static objects. This feature enables the system for smart operation through which it can diagnose itself and correct readings automatically. Any capacitance value can be represented by the reference capacitor by adjusting the attenuation of an excitation signal and the attenuation of a balance signal.

The interactive design also enables accurate measurements of capacitances by comparing measured values to parameters of the reference capacitor. This step involves back calculation utilizing parameters of the reference capacitor. The design also enables a user to eliminate static or non-varying components of a signal by adjusting the balance signal manually.

The interactive design of the present invention also enables measuring of capacitance signals from an Adaptive Electrical Capacitance Volume Tomography (AECVT) sensor. Different configurations of circuits that involve attenuators to excitation channels, filters, phase shifters, and multiple frequency excitations are preferably used. In AECVT, segments of a capacitance plate are addressed with different voltage levels and phase shifts to focus and steer capacitance sensitivity of a plate configuration. Relative electric field intensity in the imaging domain of an AECVT sensor determines sensitivity of the sensor's capacitance measurements at regions in the imaging domain to perturbations in dielectric material. Those perturbations, collectively, establish a sensitivity map tying the sensors measured capacitances to distribution of dielectric material. In AECVT, the sensitivity distribution can be zoomed or steered by focusing and moving the electric field between the sensor plates to regions where higher resolution is required. This is preferably achieved by applying voltages of different amplitudes and phase shifts to segments of an AECVT sensor. Different amplitudes are used to focus the electric field distribution and different phase shifts are for steering the focus of an electric field distribution. DAS design in the present invention establishes circuit diagrams that can achieve this functionality. Different arrangements can be established to enable capacitance measurements of an adaptive plate combination.

One embodiment circuit configuration involves using an attenuator to inject different signal amplitudes at different excitation segments of a plate and adding collective responses from each receiver segment.

Another embodiment circuit involves using a decoder to time the excitation of excitation segments and to store responses of receiver segments in a delay. All delays from receiver segments are then added for the collective response of adaptive plate segments. This configuration enables isolation of cross excitation segment interference and allows independent interrogation of certain segments in the adaptive plate. When all excitation segments are activated at the same time, a current path exists between one excitation segment to all receiver segments directly and through other excitation segments. This design enables selection of excitation and receiver segments while isolating the cross excitation effect by grounding or isolating all other excitation segments while the segment of interest is excited.

Another circuit embodiment involves using an attenuator to inject different signal frequencies at different excitation segments of a plate and adding collective responses from each receiver segment after a band pass filter (BPF) and independent receiver circuits. Here, different excitation frequencies are used to isolate each segment interaction with receiver segments. In the prior art, multiple excitation frequencies are used to increase data acquisition speed. Each excitation is passed through a filter bank to detect one capacitance reading. In the present invention, responses from all frequencies are preferably added together after the receiver segments circuitry to measure collective capacitance of an adaptive sensor.

Another circuit embodiment involves using an attenuator to inject different excitation frequencies to interrogate the same capacitance represented by the same plate. Here, different frequencies are used to image materials with dielectric constants that respond differently to excitation from different frequencies. Capacitance measurements from each frequency are used to produce different images of the material at different frequencies. Collecting the response of material to different frequencies is a new added dimension that is used for higher resolution imaging. For example, human tissue is an example of a material that responds differently at different frequencies.

Another circuit embodiment involves using an attenuator and phase shifter to inject different signal amplitudes and phases at different excitation segments of a plate and adding the collective response from all receiver segments. Phase shifts at each segment are preferably used to steer a sensitivity beam of an adaptive plate combination.

The interactive design of the present invention also preferably enables detection of parameters for active electricity in the imaging domain. Active electricity represents charges passing through the imaging domain (e.g., static charge buildup in a moving flow), voltage and current pulses in the imaging domain (e.g., electric activity in a biological organ or tissue), ionization in imaging domain (e.g., ionization in combustion flames). Active electricity parameters include frequency, charge distribution, voltage amplitude, and current amplitude. This is preferably achieved through the use of multiple excitation frequencies or sweep frequency excitation, tunable band pass filters at receiver channels, and an ECVT sensor to detect and image active electricity.

The response of different plate combinations of a capacitance tomography sensor is used to determine location and amplitude of active electricity. Collective capacitance measurements are used to image the location of active electricity as active electricity has a similar effect on measured capacitance as change in material distribution. Employing similar reconstruction algorithms, it is possible to visualize where in the imaging domain the active electricity is coming from. Interactive phase control of the detector signal in the current interactive data acquisition system is used to determine the phase of active electricity in imaging domain. In this case, measurements of active electricity are maximized by matching phase shifts of excitation and demodulation signals to that of active electricity. Detection of active electricity is performed by incrementally changing the phase of excitation until maximum response of capacitance measurement is reached. At that point, the phase of the excitation signal is equal to the phase of the active electricity. When the phase of the active electricity and excitation signal match, response from a capacitance sensor will be maximized. To find the maximum responses, the phase of the excitation signal (because it can be controlled) is changed until the maximum response is found. At this point, the phase of the active electricity has been determined (as it matches the one found for maximum sensor response). It is possible to observe how the phase of the active electricity changes by using the previously determined value as a reference.

Sweeping excitation frequency and tunable band pass filters are preferably used to determine the frequency band and response of active electricity in the imaging domain.

The interactive design of the present invention also preferably enables the isolating of temperature influence of sensor and wall material by placing sensors of similar shape and size along walls of different thicknesses. Capacitance signals from different walls can be back calculated to solve for change in wall properties due to external elements.

In the preferred embodiment, Bayesian statistics are used to infer the nonvarying component of a capacitance signal for each plate combination in an ECT, ECVT, or AECVT sensor. Calibration of a capacitance sensor usually involves an offline step where the capacitance of an empty sensor is recorded. For online calibration of capacitance sensor, the nonvarying components of measured capacitance that correspond to static or parasitic capacitance are required so they can be eliminated and the dynamic range of the data acquisition electronics can be matched to the dynamic range needed for measurements. Bayesian prediction is based on providing a probability for the static components of measured signals so they can be compensated for. Initial estimation can be based on sensor modeling. However, due to practical conditions, modeling might not be accurate in estimating non-varying components of a capacitance measurement. Bayesian prediction enables updates of the initial estimates based on new measurements. The estimation of static components is adjusted and new measurements are acquired and the probability that those updates are accurate increases over time. This eliminates the need for calibrating the sensor offline. With Bayesian statistics, prior information is used to predict the varying component of a capacitance signal and its standard deviation. Such information is then used to set a balance signal to eliminate fixed components of capacitance measurements and focus dynamic range of data acquisition on varying components only. Discrepancies between static components measured using an interactive acquisition system and those obtained from simulations knowing the sensor design are used to reconstruct the background of flow concentration over which variation is layered. Discrepancy in capacitance is obtained by back calculation from the signal of the reference capacitor. Based on Bayesian inference of the static capacitance signal, the sensor can be in continuous mode of calibration while capturing data. Each new measurement will be used to update the Bayesian prediction.

The foregoing and other features and advantages of the present invention will be apparent from the following more detailed description of the particular embodiments, as illustrated in the accompanying drawings.

BRIEF DESCRIPTION OF THE DRAWINGS

The following detailed description of the example embodiments refers to the accompanying figures that form a part thereof. The detailed description provides explanations by way of exemplary embodiments. It is to be understood that other embodiments may be used having mechanical and electrical changes that incorporate the scope of the present invention without departing from the spirit of the invention.

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1:
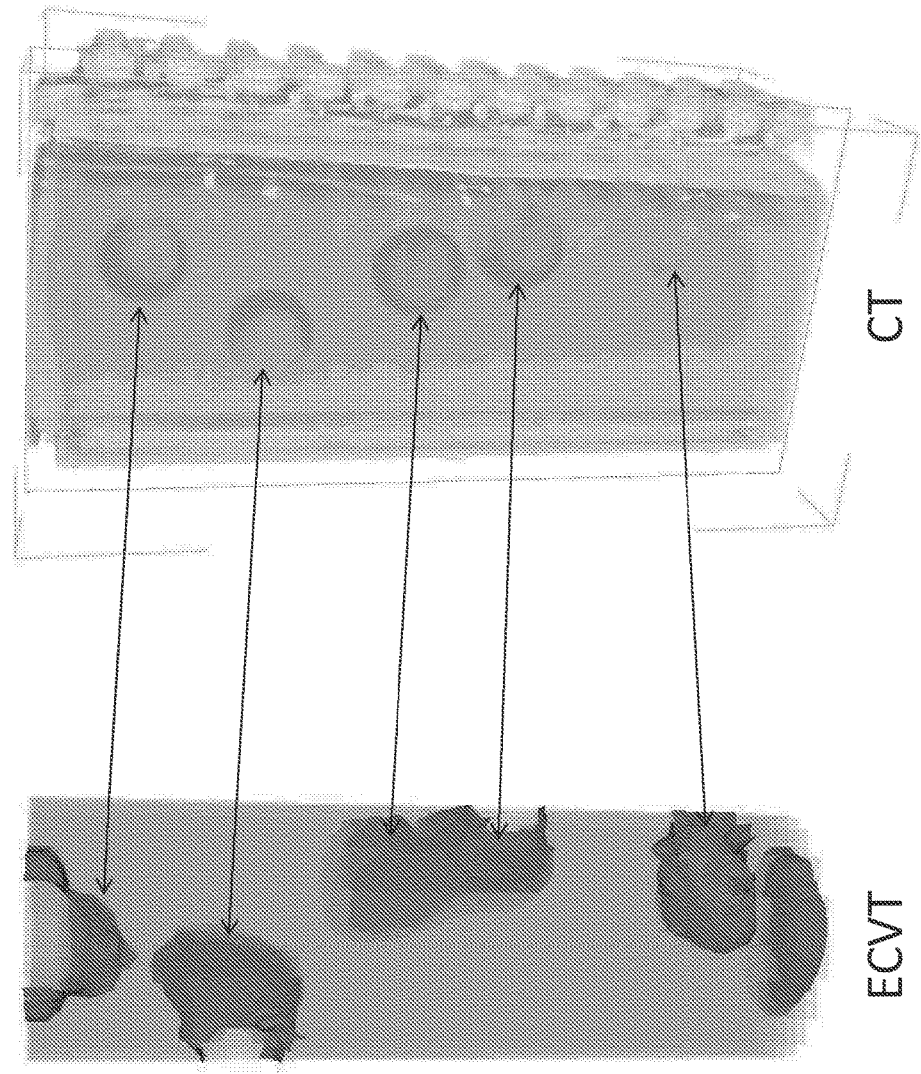
FIG. 1 depicts an example of a real-time image of voids in a bed of particles using a CT scan and an Electrical Capacitance Volume Tomography (ECVT) sensor.

FIG. 1 depicts an example of a real-time image of voids in a bed of particles using a CT scan and an Electrical Capacitance Volume Tomography (ECVT) sensor. Both CT scan image and ECVT imaging of the same structure were obtained for direct comparison. The image shows discrepancy of resolution between both imaging technologies. The left column illustrates reconstruction using ECVT of a packed bed with ping pong balls to simulate voids placed at different locations. The right column illustrates a CT scan of the ECVT system including particles, voids, column and sensors.

Figure 2:
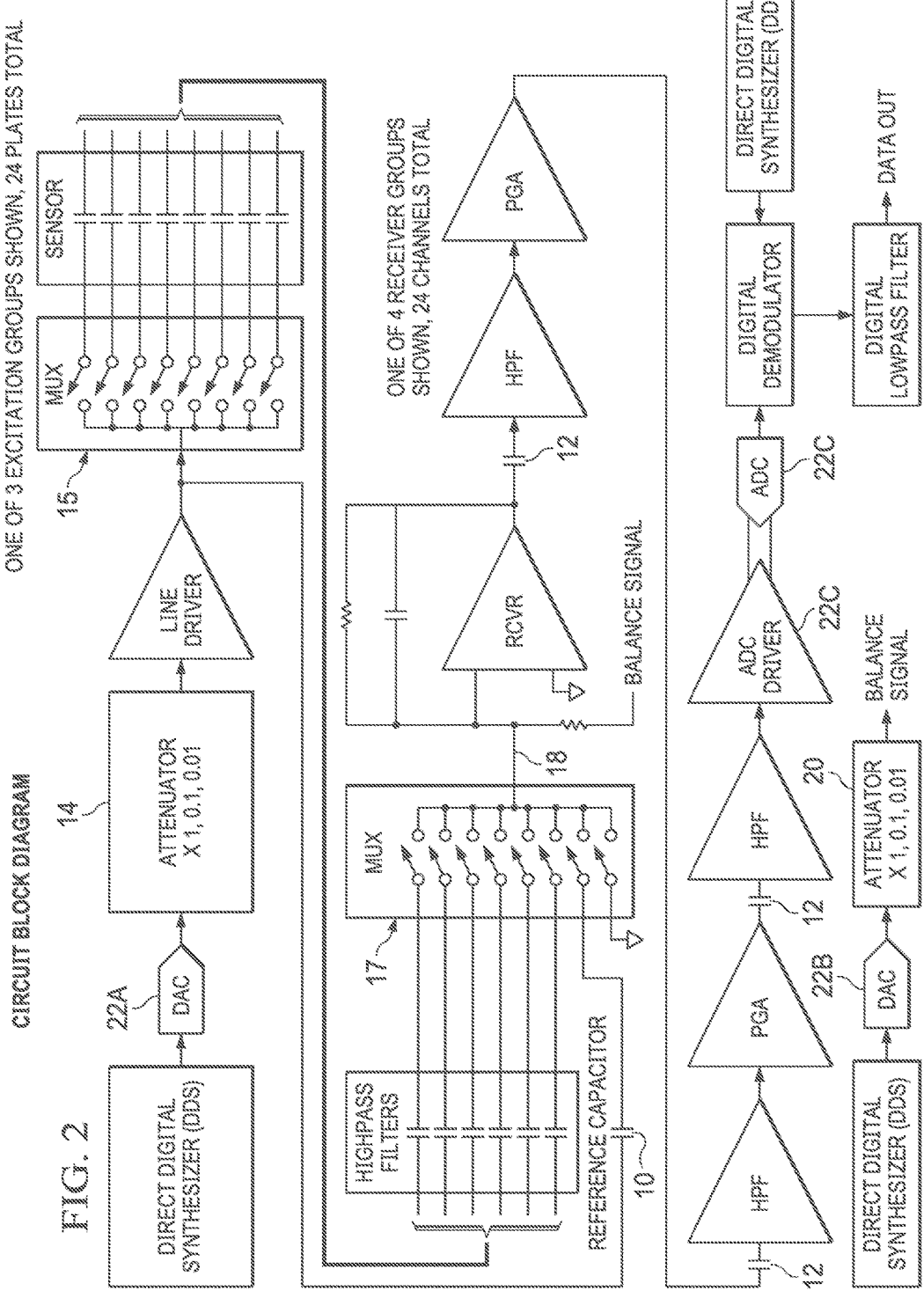
FIG. 2 illustrates one embodiment of the present invention having a sensor with up to 24 plates.

FIG. 2 illustrates one embodiment of the present invention having a sensor with up to 24 plates. More plates can be accommodated by adding more excitation and receiver groups. The embodiment of FIG. 2 is comprised of:

1) a self-calibration (or reference) capacitor (10) connected to the multiplexer input. The self-calibration capacitor can be used to test the instrument, perform automatic calibration without user involvement, compensate for long term drift and temperature variation, and provide data of virtual flows.

2) low frequency interference blocking through high pass capacitors (12) to eliminate power line frequency interference.

3) excitation attenuators (14) at excitation channels: The attenuators are preferably used to control the drive signal amplitude for materials with different dielectric constants and for simulating low capacitance values from a reference capacitor.

4) a balance signal injection point (18) at the front to maintain stability.

5) precision balance attenuators (20) preferably compatible with a wide range of dielectric constants to provide interactive control of the acquisition system.

6) a common voltage reference signal supplying excitation and balance to Digital-to-Analog Converters (DAC) (shown at (22 A, B)), and Analog-to-Digital Converters (ADC) (shown at (22C)). This makes all measurements ratiometric, cancelling out temperature drift of the reference. The common voltage reference that supplies the excitation DAC (Digital-to-Analog Converter at (22A)), the Balance DAC (at (22B)) and the ADC's (Analog-to-Digital Converter at (22C)) improves temperature stability.

The interactive design of the present invention enables self calibration by including an internal reference capacitor with a known value. The internal capacitor acts as a reference through which any capacitance measurement can be back calculated by comparing PGA, balance, phase shifts, and excitation parameters to those of the reference capacitance measurement parameters. Self calibration of a capacitance sensor can be achieved by simulating the capacitance signal of an empty sensor and adjusting parameters of data acquisition using the reference capacitor. In prior art systems, a capacitor is used to empty charges from and into a reference capacitor to compensate for parasitic capacitance. This prior art technique is different than the present invention in at least two ways: 1) it is designed for a charge/discharge acquisition system whereas present invention is AC based and 2) it uses a reference capacitor to empty or withdraw charges to compensate for parasitic capacitance whereas the present invention measures parameters of a reference capacitor through an FPGA and uses those parameters as a reference for parameters of other measured capacitances. Parameters are used to back calculate capacitance values or to set calibration parameters for a particular sensor.

The electronic multiplexer (15) can be considered a switch that connects the drive signal to each electrode (or plate) of the sensor as each electrode is selected. Accordingly, the driving signal is considered the input to the sensor in the present invention. Similarly, the multiplexer (17) at the backend is a switch that connects to another one of the selected electrodes on the sensor so that a capacitance reading can be obtained between the selected electrodes. Accordingly, in FIG. 2, the output of the backend multiplexer can be considered the output of the sensor.

The reference capacitor is connected to the output of the sensor through the same path which receiver signal comes from different channels (the output of the sensor is also referred to as the receiver signal because it is received by the data acquisition portion of the system that collects the capacitance data and reconstructs the image for the area within the sensor). The output of the reference capacitor of FIG. 2 replaces the capacitance coming from a sensor channel with a static value.

The output of the sensor is also where the balance signal is connected (18). Accordingly, the balance signal connects to every channel output signal as they are selected by the multiplexer. As the reference capacitor is connected to act as a capacitance channel, it is also connected to the sensor output through the multiplexer. The self-calibration capacitor provides a static reference. The static capacitance of the reference capacitor can be used as a reference when measuring the drift or change in signal for testing of the instrument, when performing automatic calibration without user involvement, when compensating for long term drift and temperature variation, and when providing data of virtual flows.

For example, the reference capacitor can be used in the following ways:

1—measure the static capacitance and store calibration parameters. Then perform the same thing again after a period of time. The difference between both measurements would be attributed to drift in system electronics.

2—use excitation attenuators with the static capacitor to simulate different capacitance values.

3—store actual flow patterns by representing each measured capacitance value by different level of excitation to reference capacitor. The collection of all stored excitation for capacitance values in a frame represents data for reconstruction of flow image of the stored flow.

The balance signal at the front end, and before the receiver amplifier, is used to eliminate drift in the signal due to temperature variation of the amplifier.

The present invention preferably uses a common voltage reference for supplying excitation and balance of the DAC, and ADC's. This allows for ratiometric measurements, cancelling out temperature drift of the reference. The common voltage reference is supplied to items marked as (22) in FIG. 2. ADC and DAC devices convert analog signals to digital ones and digital signals to analog ones, respectively. Reference voltage is supplied to the ADC and DAC and is used to set the voltage level. The reference voltage is used to set how much voltage is from one digital step to another in the process of converting it to or from analog. The reference voltage is the maximum value that an ADC/DAC can convert. This voltage range is divided by the DAC/ADC resolution, or steps. If two DAC or ADC are used with a different voltage reference, the step size will be different, and the same digital number would be converted to a different analog value or vice versa.

Having all ADC and DAC connected to the same reference voltage eliminates the effect of drift in the reference voltage. Since digital steps in all ADC or DAC are impacted the same because of a voltage drift, the net result is that they will be cancelled. For example, a drift in ADC will impact the digital step, when converting it back to analog, the DAC will be impacted by the same reference drift and it will cancel the total effect, thus preserving the signal.

The balance signal is added to the receiver signal before receiver amplifier (or in other words to it is added to the output of the sensor at (18) to maintain stability). Accordingly, the drift in the receiver amplifier will affect both signals, mitigating its effect on the combined signal. In the past, the balance was injected after the receiver amplifier. In such arrangements, if a drift occurs after the cell is calibrated; a drift in the amplifier will yield a non-zero balance as it only affects the output of the sensor and not the balance signal. The balance signal function cancels the empty cell output. So a drift in the receiver amplifier would affect the receiver plate signal but not the balance.

In the preferred embodiment, excitation attenuators are connected to the sensor input. The excitation attenuators at excitation channels control the drive signal for materials with different dielectric constants. The electronics can saturate if a material with high dielectric constant is used. They are brought back to the required dynamic range that matches the ADC by reducing the excitation signal using the attenuators.

Precision balance attenuators are preferably used with the present invention that are compatible with wide range of dielectric constants to provide interactive control of acquisition system. The balance attenuator is implemented in two ways: 1—through a multiplexer of voltage dividers in block 20 of FIG. 2, and 2—digitally in the DDS. Similarly, the balance also preferably needs to be attenuated with precision to match the receiver signal and cancel out the empty cell output (e.g., empty column signal).

Figure 3:
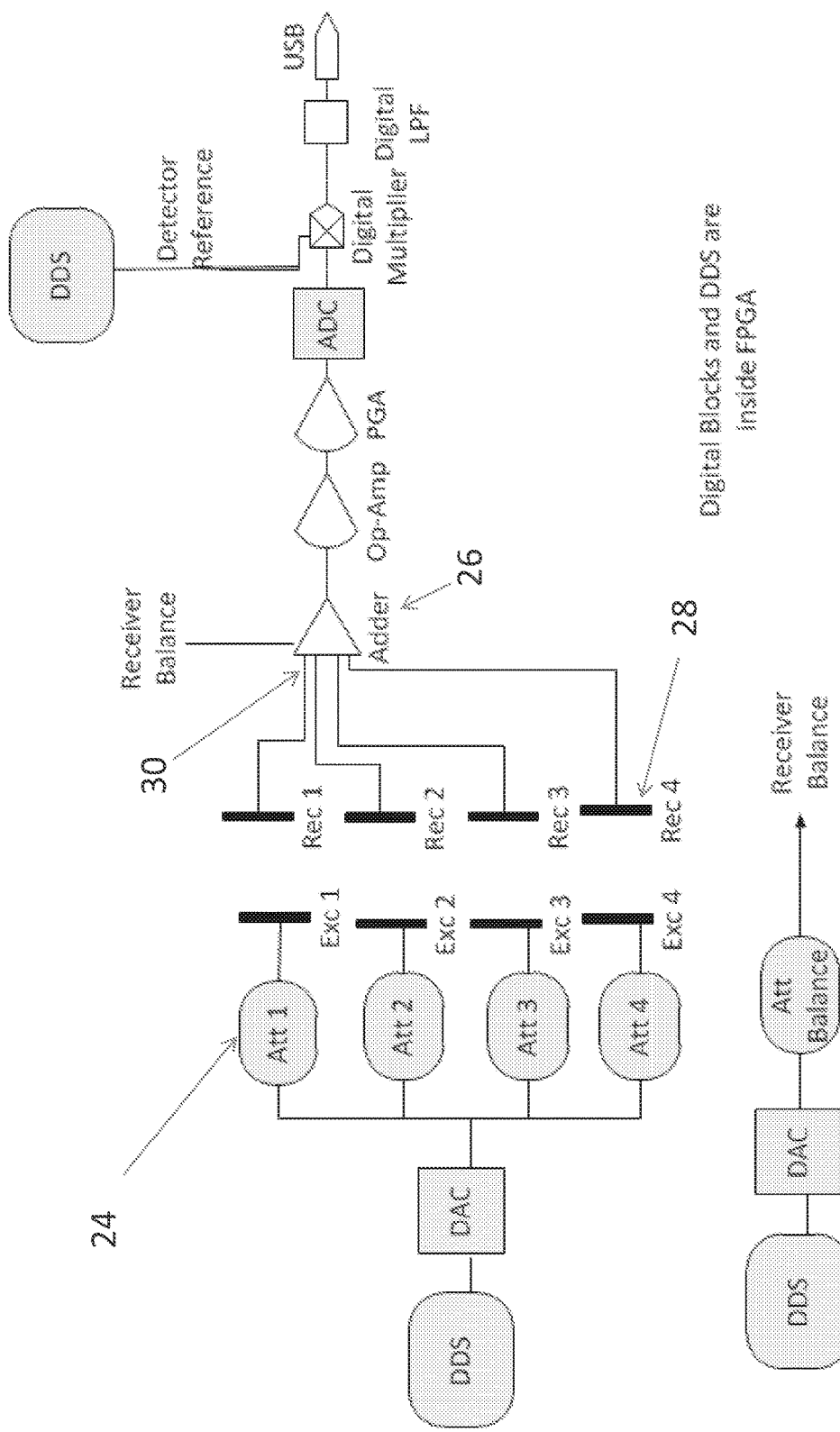
FIG. 3 illustrates an exemplary circuit embodiment for single excitation and receiver channels to measure the capacitance of adaptive sensor segments for single capacitance measurements.

FIG. 3 illustrates an exemplary circuit embodiment for single excitation and receiver channels to measure the capacitance of adaptive sensor segments for single capacitance measurements. In the following figures, the parallel lines labeled "Exc(n)" and "Rec(n)" represent capacitance segments of the sensors of the present invention. A segment in a plate is a small element that can be excited with different levels of voltage and degrees of phase. An adaptive plate is composed of a number of segments, each excited independently. Collective response of "segments" at the receiver end represent an adaptive receiver plate. This building block can be used with other circuit components like FIG. 2 to form a full system to measure multiple capacitance values of an AECVT sensor. Special features of this circuit are: 1) an attenuator (24) is used with each segment to provide control over voltage level; 2) signals are added (26) after the receiver (28) from each receiving segment; 3) signals (30) are preferably processed as a single capacitance value.

Figure 4:
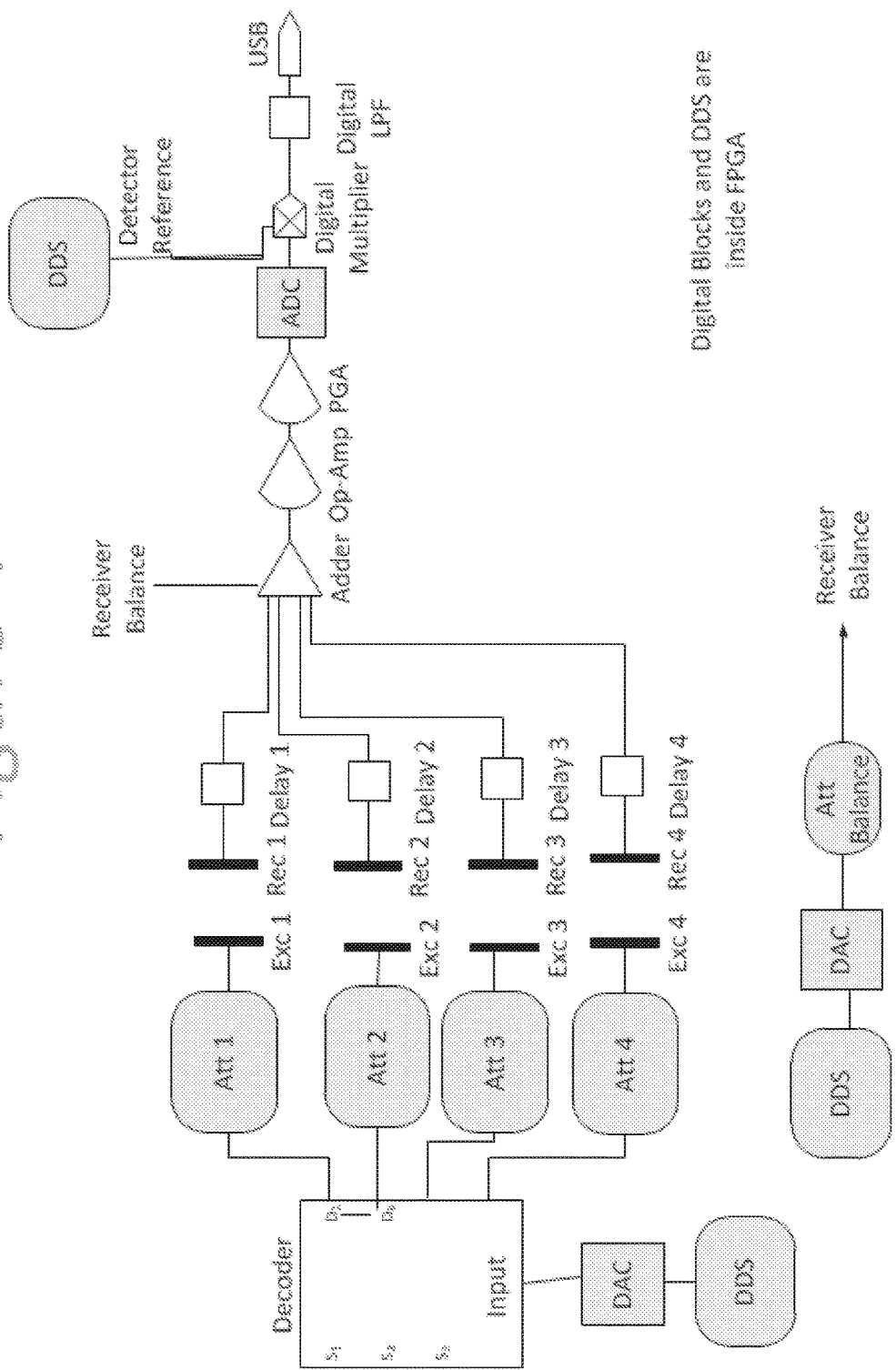
FIG. 4 illustrates an exemplary circuit embodiment for single excitation and receiver channels for measuring the capacitance of adaptive sensor segments for single capacitance measurements.

FIG. 4 illustrates an exemplary circuit embodiment for single excitation and receiver channels for measuring the capacitance of adaptive sensor segments for single capacitance measurements. This building block can be used with other circuit components like FIG. 2 to form a full system to measure multiple capacitance values of an AECVT sensor. This building block features:

1) time division to isolate cross-excitation segment capacitance contribution to the total added capacitance signal.

2) activating each segment in a different time slot and storing its receiver value in a delay for later retrieval (when a segment is excited, all other sending segments are grounded and one receiver signal is activated at a time).

3) adding all receiver signals after all excitation segments are addressed.

4) since each receiver signal is measured independently at a different time, the added receiver signal represents the weight of each independent capacitance measurement at different time slots.

Figure 5:
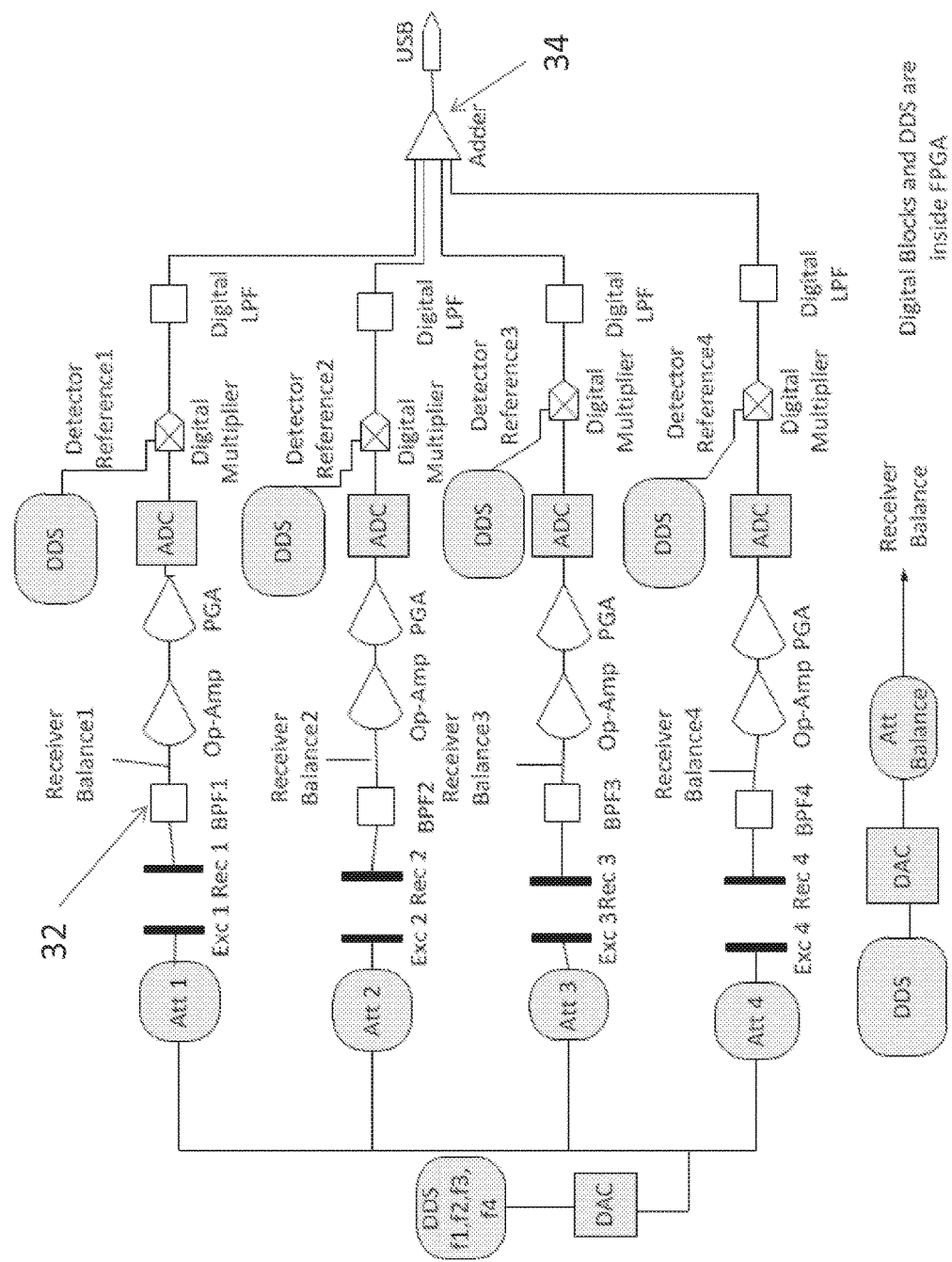
FIG. 5 illustrates one embodiment circuit for single excitation and receiver channels for measuring the capacitance of adaptive sensor segments for single capacitance measurements.

FIG. 5 illustrates one embodiment circuit for single excitation and receiver channels for measuring the capacitance of adaptive sensor segments for single capacitance measurements. This building block can be used with other circuit components like FIG. 2 to form a full system to measure multiple capacitance values of an AECVT sensor. This building block features:

1) each segment is activated with multiple frequencies independently.

2) band pass filters (32) determine each receiver's excitation channel. (Receiver signals are added (34) after demodulation to isolate frequency factors for different capacitors).

3) each receiver channel reacts to all excitation channels for that specific frequency. This is different than the prior art as signals from different frequencies here are meant to implement adaptive signals by adding all receiver channels together. In the prior art, each frequency addresses a combination of excitation and receiver plates independently. In the present invention, collective responses from all segments are added to together.

Figure 6:
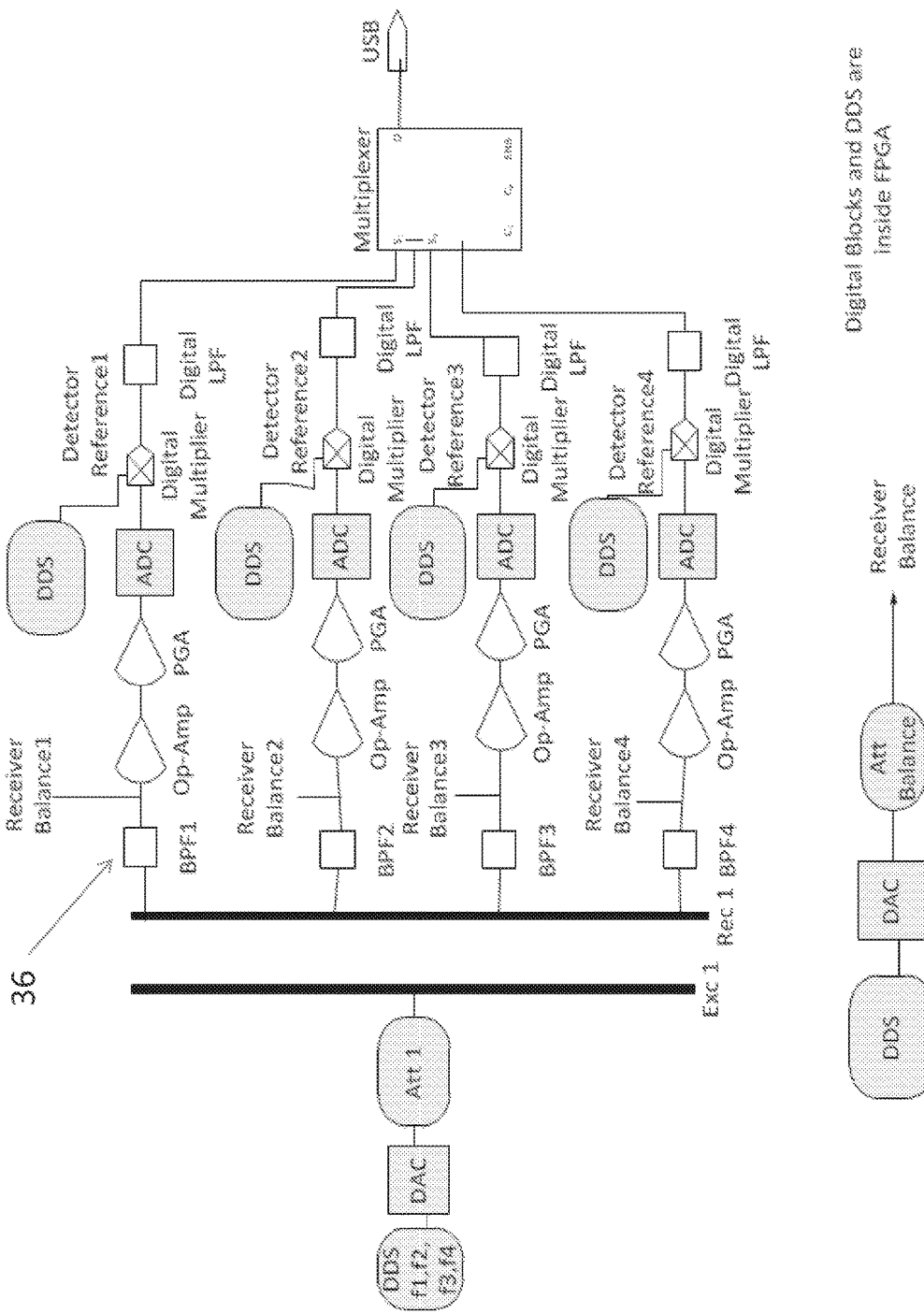
FIG. 6 illustrates an exemplary circuit is for single excitation and receiver channels for measuring the capacitance of ECVT sensors for single capacitance measurements.

FIG. 6 illustrates an exemplary circuit is for single excitation and receiver channels for measuring the capacitance of ECVT sensors for single capacitance measurements. This building block can be used with other circuit components like FIG. 2 to form a full system to measure multiple capacitance values of an AECVT sensor. This building block features:

1) an excitation signal is activated with multiple frequencies simultaneously and received from one receiver plate to multiple receiver channels through BPF's (36).

2) this allows a degree of freedom in measured data related to capacitance change at different frequencies. Materials have different dielectric constant at different frequencies and temperatures.

Figure 7:
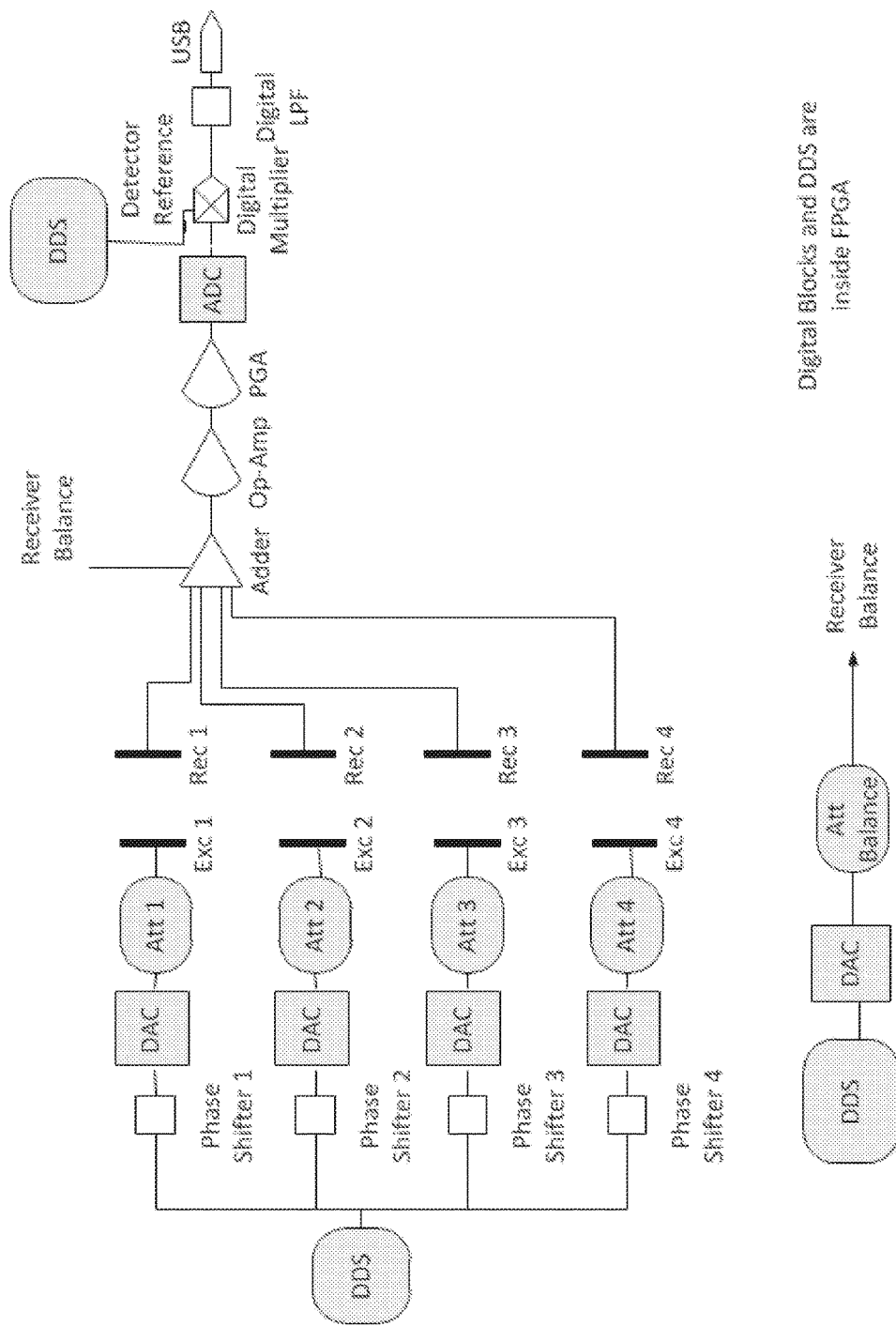
FIG. 7 illustrates an exemplary circuit for single excitation and receiver channels for measuring capacitance of adaptive sensor segments for single capacitance measurements.

FIG. 7 illustrates an exemplary circuit for single excitation and receiver channels for measuring capacitance of adaptive sensor segments for single capacitance measurements. This building block can be used with other circuit components like FIG. 2 to form a full system to measure multiple capacitance values of an AECVT sensor. This building block features:

1) providing different phase shifts for different excitation signals.

2) phase shifts can be used to steer equivalent electric field distribution to steer a sensitivity matrix distribution. This feature enables focus and zooming in an AECVT sensor.

Figure 8:
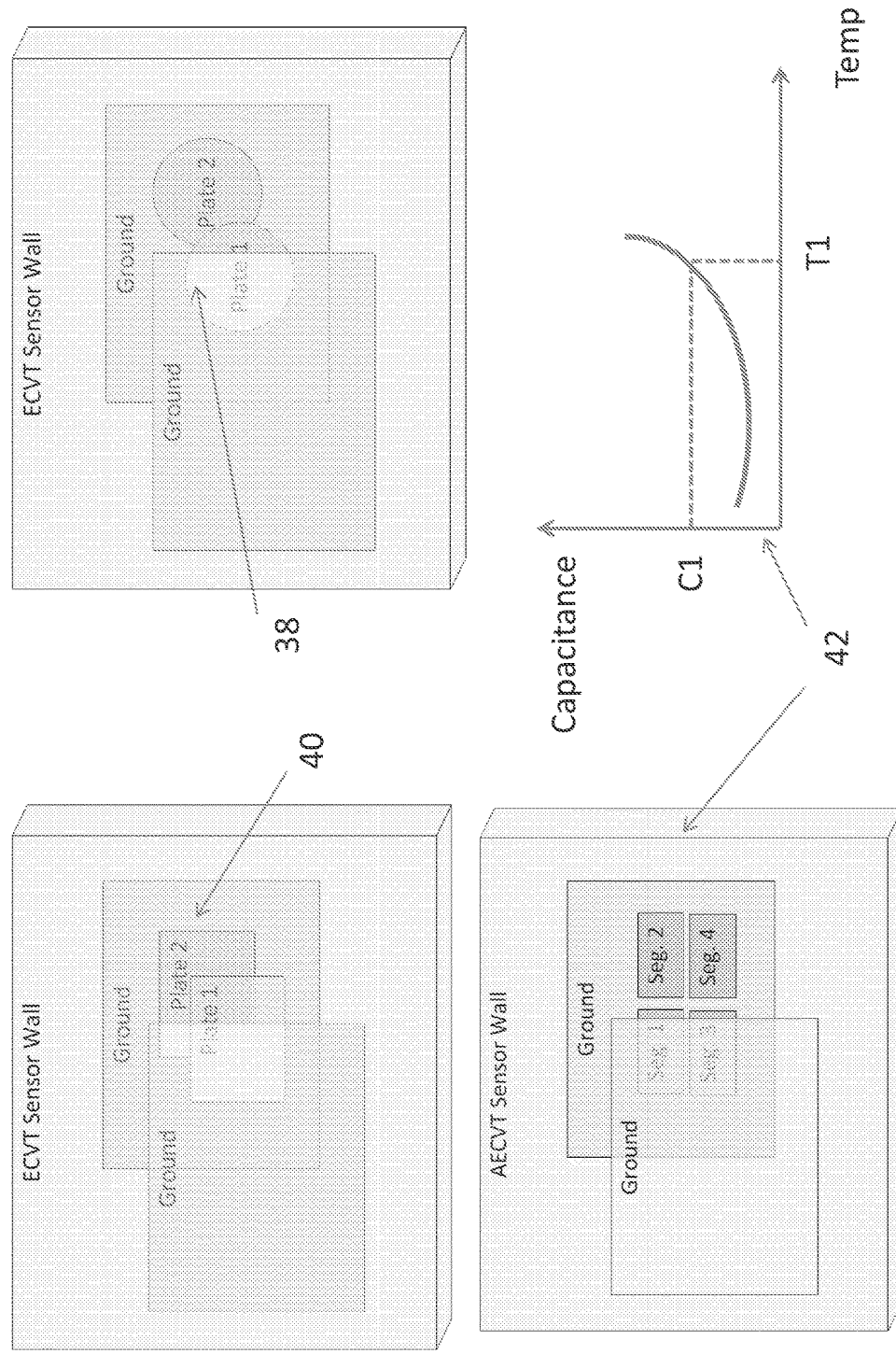
FIG. 8 is a 3D depiction of exemplary capacitance sensors for temperature measurements.

FIG. 8 is a 3D depiction of exemplary capacitance sensors for temperature measurements. As sensor plate shapes (38) and orientation may affect temperature response in measured capacitance, different temperature sensing plates may be employed to mimic shape and orientation of ECVT sensor plates for better mapping of temperature effect. Sensors (40) are used to establish a temperature profile for each plate combination in the capacitance sensor. Temperature measurements may be collected by:

1) establishing a lookup table or graph for capacitance change of empty column to temperature for each sensor plate combination embedded in a column wall (42).

2) embedding a temperature sensor in the wall to measure temperature and changing balance signal to account for static change (allowing interactive control).

3) using multiple plates embedded in the column wall to measure temperature in the wall by comparing their capacitance to a reference capacitance. A lookup table is preferably used to lookup capacitance change associated with measured temperature and compensate through balance signal.

4) compensating for effect of temperature on capacitance change due to plate expansion/deformation from that due to flow variation (because the effect of flow variation and that of temperature change in the sensor material are embedded in the same capacitance measurements, it is of interest to isolate the portion of the measured capacitance that is due to flow changes from that which is caused by the sensor plates or from the refractory material changing temperature). This can be established by measuring capacitance variation of an empty sensor at different temperatures. The lookup table can then be used to estimate temperature and capacitance change of an empty sensor. This estimation is used to compensate for changes in capacitance measurement that are due to temperature change in the sensor itself, thus the new compensated capacitance measurement will only represent change in the flow (not sensor temperature) so flow can be imaged accurately. This process isolates capacitance change of temperature variation due to flow from that due to the sensor.

The capacitance measurement from the reference capacitor can also be used to autocorrect online imaging. In online imaging, volume images are directly provided to the user by embedding the reconstruction algorithm in the FPGA. The system applies previously recorded parameters of static objects to reference capacitors to emulate a static object online. Discrepancies in reconstruction of emulated capacitance and images of static objects are then used to recalibrate the data acquisition system.

Figure 9:
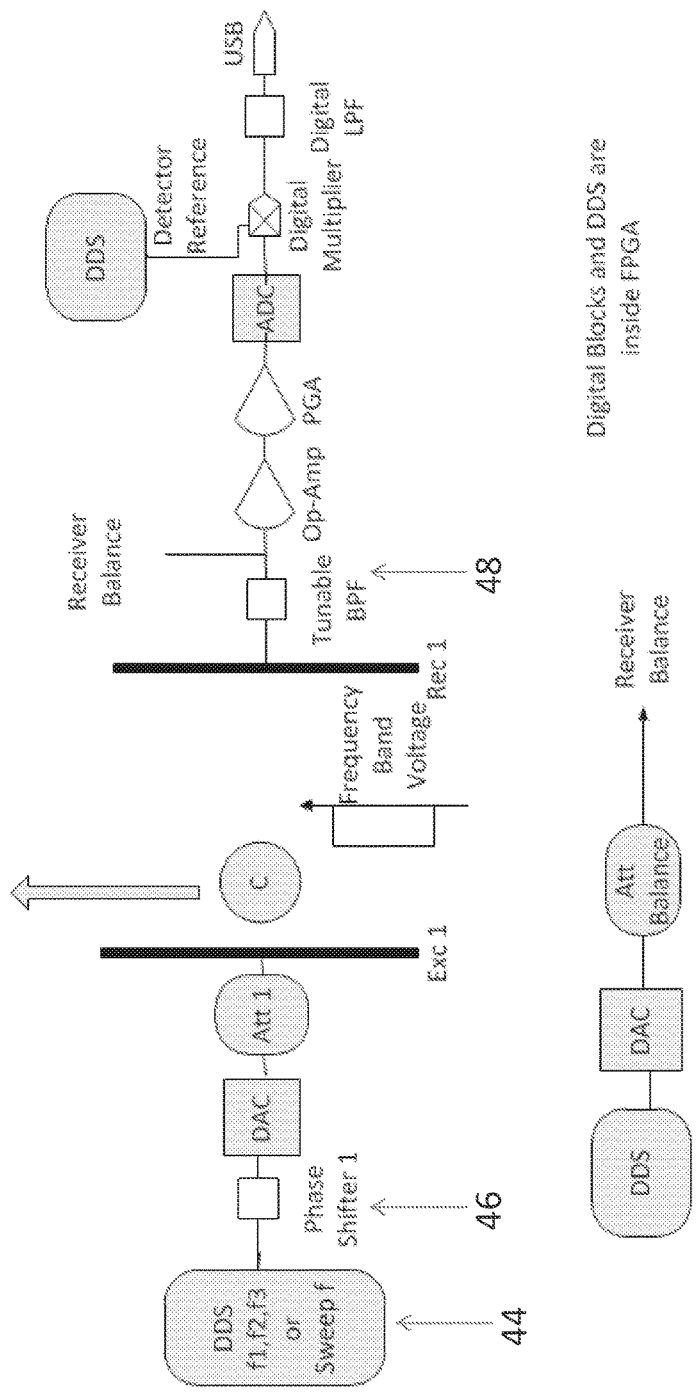
FIG. 9 is an exemplary embodiment for single excitation and receiver channels for measuring capacitance of active electricity for single capacitance measurements.

FIG. 9 is an exemplary embodiment for single excitation and receiver channels for measuring capacitance of active electricity for single capacitance measurements. This building block can be used with other circuit components like FIG. 2 to form a full system to measure multiple capacitance values of an ECVT sensor. This building block features:

1) multiple frequency excitation or sweep excitation of plates, attenuator (44) for control of excitation amplitude and phase shifter (46) for control of excitation phase.

2) tunable Band Pass Filters (BPF) (48) to identify frequency of active electricity in imaging domain. The phase shifter in excitation channels is used to synchronize with active electricity for maximum signal output.

3) the attenuator is used to measure active electricity amplitude.

4) sweep frequency and tunable BPF are to identify frequency range of active electricity in the imaging domain.

5) collective measurements from ECVT sensor plates are to be used to reconstruct location of active electricity in the imaging domain.

Figure 10:
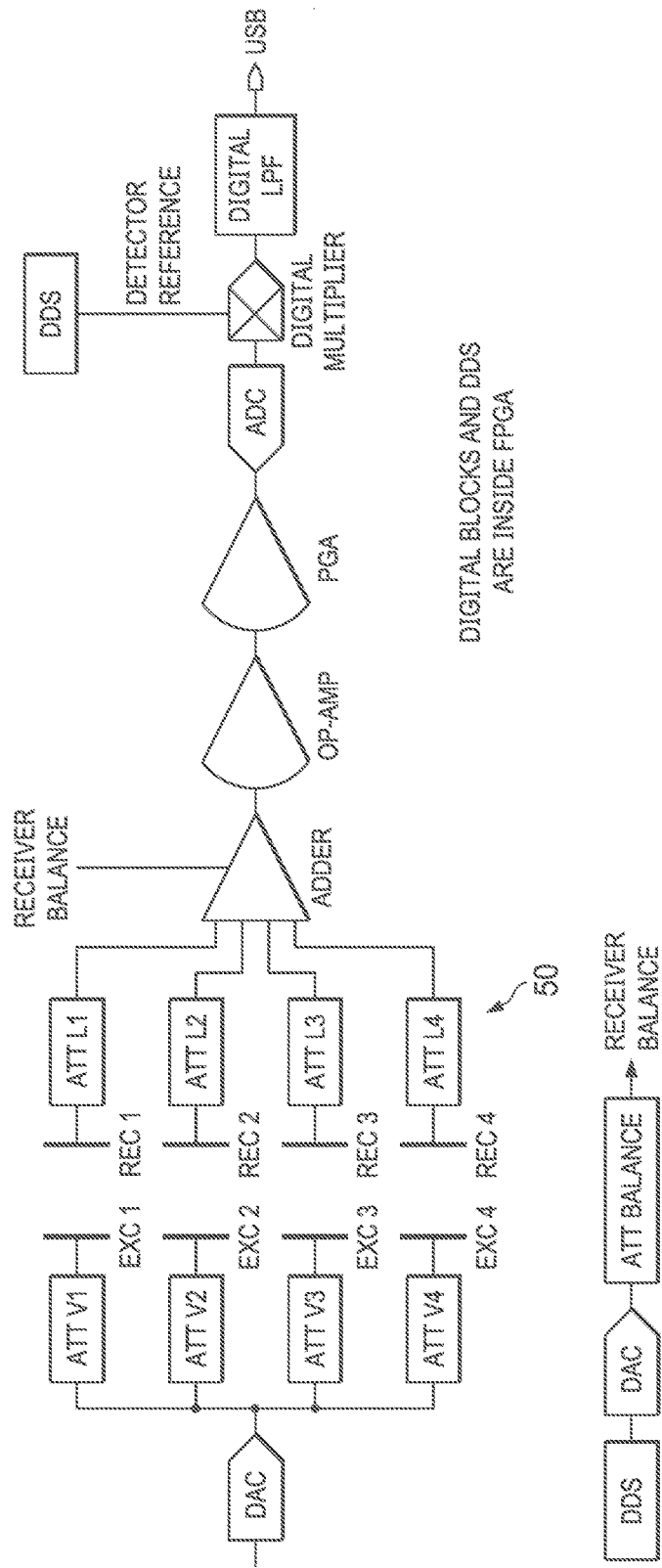
FIG. 10 illustrates an exemplary embodiment for single excitation and receiver channels for measuring capacitance of adaptive sensor segments for single capacitance measurements.

FIG. 10 illustrates an exemplary embodiment for single excitation and receiver channels for measuring capacitance of adaptive sensor segments for single capacitance measurements. This building block can be used with other circuit components like FIG. 2 to form a full system to measure multiple capacitance values of an AECVT sensor. This building block features:

1) current attenuator (50) located after receiver segments for assigning different weights to currents from different receiver segments.

2) the current attenuators are used to shape the sensitivity of the adaptive sensor by combing receiver segments with different weights.

Figure 11:
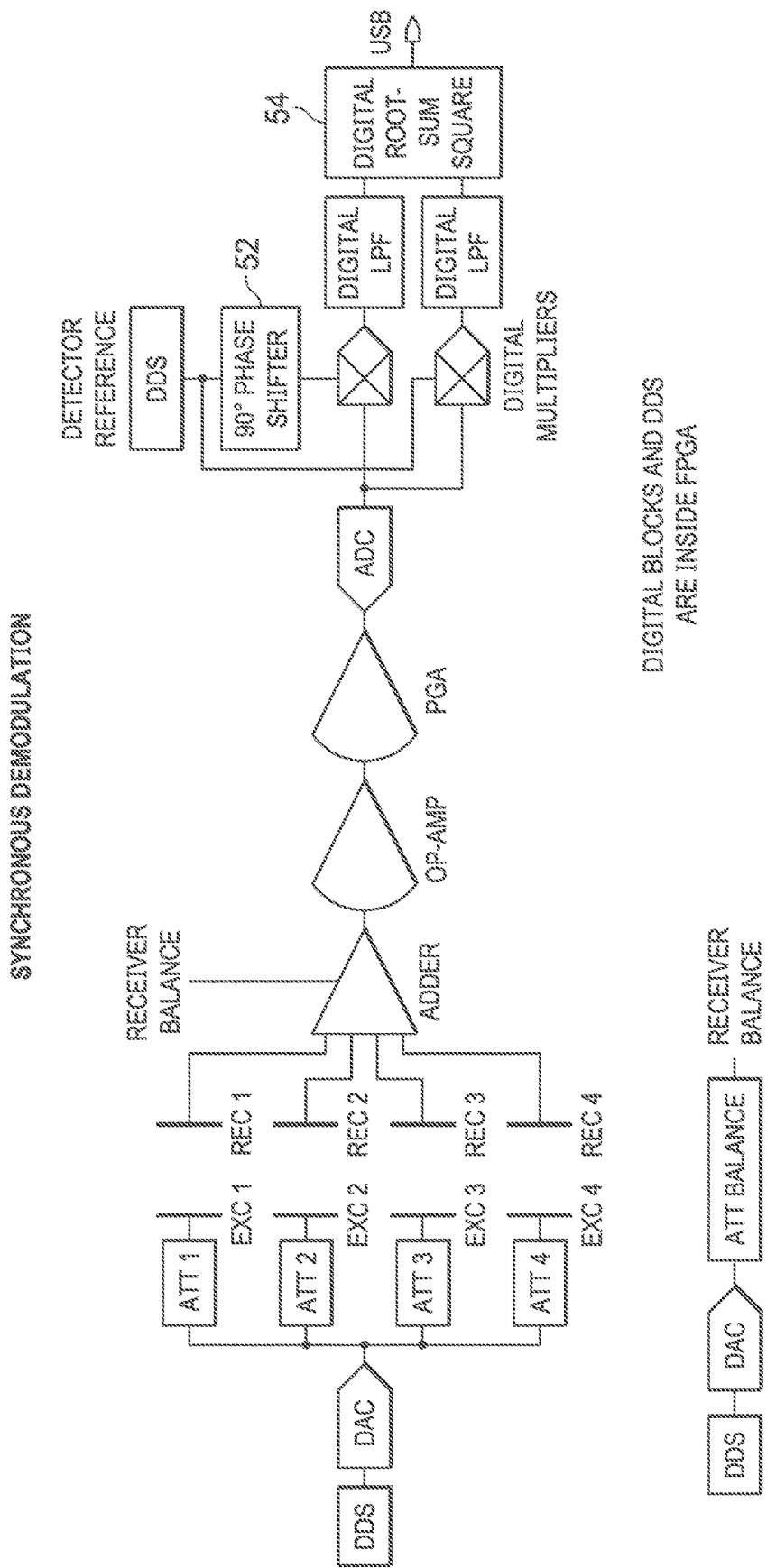
FIG. 11 illustrates an exemplary embodiment for single excitation and receiver channels to measure capacitance of adaptive sensor segments for single capacitance measurements.

FIG. 11 illustrates an exemplary embodiment for single excitation and receiver channels to measure capacitance of adaptive sensor segments for single capacitance measurements. This building block can be used with other circuit components like FIG. 2 to form a full system to measure multiple capacitance values of an AECVT sensor. This building block features:

1) on-phase and quadrature parallel detectors followed by a root-sum-square magnitude summation (54). A 90 degree phase shifter (52) provides the reference signal for the quadrature detector.

2) the phase of the detected signal is the arctangent of the in-phase and quadrature components.

3) detected signal phase is used to represent dielectric and conductive material properties in a dual-modality mode. Phase of the detected signal in dual-modality is compared to phase of a calibrated signal to decouple material in the imaging domain from its conductive and dielectric properties.

In an exemplary embodiment of the invention, synchronous detection of the signal after the receiver amplifier is provided using a detector reference and its 90 degree phase shifted complement. The detector reference and its 90 degrees phase shifted complement are multiplied separately with the signal from receiver amplifier. The magnitude of the signal is the root-sum-square summation of the in-phase and 90 degree quadrature components. The phase of the signal is the arctangent of the in-phase and quadrature components. The synchronous detector is used during imaging operation and is also used during the calibration process of the data acquisition system.

The present invention also preferably includes a redundant plate measurement technique. Typically in capacitance measuring devices, the capacitance between two plates is considered to be the same regardless which of the two plates is considered a sender and which is considered a receiver. In the present invention a distinction is established and a capacitance between two pair of plates is calibrated and measured with each plate acting as a receiver and the other plate as sender in one arrangement, and vise versa in another arrangement. The final capacitance is a weighted average of the two measured capacitance values for the same pair of plates. A determination if the two redundant values are weighted equally or not is determined depending on sensor design.

While certain embodiments of the present invention are described in detail above, the scope of the invention is not to be considered limited by such disclosure, and modifications are possible without departing from the spirit of the invention as evidenced by the following claims.

What is claimed is:

1. A system for generating a three-dimensional tomograph of a vessel interior or other object, the system comprising:
   a three-dimensional capacitance sensor device comprising a plurality of electrodes for placement around the vessel or the object, wherein the three-dimensional capacitance sensor device is adapted to provide electric field distribution and sensor sensitivity in three geometric dimensions, wherein the three-dimensional capacitance sensor device has an input and an output;
   a reference capacitor electrically connected to the input of the three-dimensional capacitance sensor device;
   data acquisition electronics in communication with the output of the three-dimensional capacitance sensor device for receiving input data from the three-dimensional capacitance sensor device and in communication with the reference capacitor for obtaining the capacitance measurement of the reference capacitor;
   a processing system in communication with the data acquisition electronics, the processing system programmed with instructions for executing on the processing system to:
   a.) use the capacitance measurement of the reference capacitor as a reference for calibration of the system;

b.) calibrate the system based on the capacitance measurement of the reference capacitor and use the capacitance measurement of the reference capacitor to back calculate capacitance values or to set calibration parameters for the three-dimensional capacitance sensor device; and c.) reconstruct a three-dimensional volume-image from the input data collected by the data acquisition electronics.

2. A system according to claim 1, wherein the three-dimensional capacitance sensor device is an adaptive electrical capacitance volume tomography sensor device and wherein the plurality of electrodes are each comprised of a plurality of capacitance segments; and wherein the plurality of capacitance segments of at least one electrode are individually addressable with voltages.

3. A system according to claim 1, further comprising:

a balance signal line electrically connected to the output of the three-dimensional sensor for providing a balance signal to the system to mitigate the effect of drift;

a receiver amplifier having an input and output, wherein the input of the receiver amplifier is electrically connected with the output of the three-dimensional sensor and wherein the output of the receiver amplifier is in electrical communication with the data acquisition electronics.

4. A system according to claim 3, further comprising:

a precision balance attenuator electrically connected to the balance signal line to provide interactive control of the system.

5. A system according to claim 4, further comprising:

a first digital-to-analog converter in electrical communication with the input of the three-dimensional capacitance sensor device;

a first analog-to-digital converter in electrical communication with the output of the three-dimensional sensor;

a second digital-to-analog converter in electrical communication with the precision balance attenuator; and a common voltage reference electrically connected to the first and second digital-to-analog converter and the first analog-to-digital converter to eliminate the effect of drift.

6. A system according to any one of claim 4, further comprising:

reference plates embedded into walls of the three-dimensional capacitance sensor device; and wherein the processing system is programmed with instructions for executing on the processing system to: a.) determine temperature characteristics based on changes in capacitance of the reference plates; and b.) tune the three-dimensional capacitance sensor device based on the temperature characteristics.

7. A system according to any one of claims 1 and 4, further comprising:

an excitation attenuator in electrical communication with the input of the three-dimensional capacitance sensor device to provide control over the electronic signaling to the input of the three-dimensional capacitance sensor.

8. A system according to claim 7, wherein the excitation attenuator is controlled based on the dielectric constant of a material used with the system.

9. A system according to claim 1, wherein the processing system is programmed with instructions for executing on the processing system to:

store measured capacitances between a first and second electrode of the three-dimensional capacitance sensor device, wherein a first stored measured capacitance is the capacitance with the first electrode as a sending electrode and the second electrode as a receiving electrode, wherein a second stored measured capacitance is the capacitance with the second electrode as the sending electrode and the first electrode as the receiving electrode; and determining a final capacitance as a weighted average of the first and second stored measured capacitances of the first and second electrodes.

10. A system according to claim 1, wherein the processing system is programmed with instructions for executing on the processing system to: calibrate the system using Bayesian statistical prediction.

11. A system according to claim 1, wherein the processing system is programmed with instructions for executing on the processing system to: a.) store data collected from the three-dimensional capacitance sensor device; b.) use the stored data to predict a varying component of a capacitance signal using Bayesian statistical modeling.

12. A system according to claim 11, wherein the processing system is programmed with instructions for executing on the processing system to: set a balance signal to eliminate fixed components of capacitance measurements from the three-dimensional capacitance sensor device.

13. A system according to claim 1, wherein the three-dimensional capacitance sensor device is an adaptive electrical capacitance volume tomography sensor device and wherein the plurality of electrodes are each comprised of a plurality of capacitance segments;

wherein the plurality of capacitance segments of at least one electrode are individually addressable with voltages, the system further comprising:

a plurality of analog and Direct Digital Synthesis (DDS) attenuators in electrical communication with the plurality of capacitance segments for controlling voltage on the capacitance segments.

14. A system according to claim 1, wherein the three-dimensional capacitance sensor device is an adaptive electrical capacitance volume tomography sensor device and wherein the plurality of electrodes are each comprised of a plurality of capacitance segments;

wherein the plurality of capacitance segments of at least one electrode are individually addressable with voltages, the system further comprising:

a plurality of analog and phase shifters in electrical communication with the plurality of capacitance segments for controlling voltage on the capacitance segments.

15. A system according to claim 1, wherein the three-dimensional capacitance sensor device is an adaptive electrical capacitance volume tomography sensor device and wherein the plurality of electrodes are each comprised of a plurality of capacitance segments;

wherein the plurality of capacitance segments of at least one electrode are individually addressable with voltages, the system further comprising:

a tunable band pass filter in electrical communication with the output of the three-dimensional capacitance sensor device; and wherein the processing system is programmed with instructions for executing on the processing system to identify a location of active electricity within the three-dimensional capacitance sensor device.

16. A system according to claim 15, further comprising:
a phase shifter in electrical communication with the input of the three-dimensional capacitance sensor device for synchronizing with the active electricity; and
an attenuator in electrical communication with the input of the three-dimensional capacitance sensor device for detecting an amplitude of active electricity.

17. A system according to claim 1, wherein the processing system is programmed with instructions for executing on the processing system to use the capacitance measurement from the reference capacitor to autocorrect online imaging.

18. A system for generating a three-dimensional tomograph of a vessel interior or other object, the system comprising:
a three-dimensional capacitance sensor device comprising a plurality of electrodes for placement around the vessel or the object, wherein the three-dimensional capacitance sensor device is adapted to provide electric field distribution and sensor sensitivity in three geometric dimensions, wherein the three-dimensional capacitance sensor has an input and an output;
data acquisition electronics in communication with the output of the three-dimensional capacitance sensor device for receiving input data from the three-dimensional capacitance sensor device; and
a processing system in communication with the data acquisition electronics, the processing system programmed with instructions for executing on the processing system to reconstruct a three-dimensional volume-image from the input data collected by the data acquisition electronics;
wherein the three-dimensional capacitance sensor device is an adaptive electrical capacitance volume tomography sensor device and wherein the plurality of electrodes are each comprised of a plurality of capacitance segments;
wherein the plurality of capacitance segments of at least one electrode are individually addressable with voltages, the system further comprising:
a tunable band pass filter in electrical communication with the output of the three-dimensional capacitance sensor device;
a phase shifter in electrical communication with the input of the three-dimensional capacitance sensor device for synchronizing with the active electricity;
an attenuator in electrical communication with the input of the three-dimensional capacitance sensor device detecting an amplitude of active electricity; and
wherein the processing system is programmed with instructions for executing on the processing system to identify a location of active electricity within the three-dimensional capacitance sensor device.

19. A system according to claim 18, further comprising:
a reference capacitor of a fixed predetermined value electrically connected to the input of the three-dimensional capacitance sensor device and wherein the data acquisition system is in electrical communication with the reference capacitor for obtaining the capacitance measurement of the reference capacitor;
wherein the processing system is programmed with instructions for executing on the processing system to:
a.) use the capacitance measurement of the reference capacitor as a reference for calibration of the system; and
b.) calibrate the system based on the capacitance measurement of the reference capacitor and use the capacitance measurement of the reference capacitor to back calculate capacitance values or to set calibration parameters for the three-dimensional capacitance sensor device.

20. A system for generating a three-dimensional tomograph of a vessel interior or other object, the system comprising:
a three-dimensional capacitance sensor device comprising a plurality of electrodes for placement around the vessel or the object, wherein the three-dimensional capacitance sensor device is adapted to provide electric field distribution and sensor sensitivity in three geometric dimensions, wherein the three-dimensional capacitance sensor device has an input and an output;
a reference capacitor electrically connected to the input of the three-dimensional capacitance sensor device;
data acquisition electronics in communication with the output of the three-dimensional capacitance sensor device for receiving input data from the three-dimensional capacitance sensor device and in communication with the reference capacitor for obtaining the capacitance measurement of the reference capacitor;
a processing system in communication with the data acquisition electronics, the processing system programmed with instructions for executing on the processing system to:
a.) use the capacitance measurement of the reference capacitor as a reference for calibration of the system;
b.) calibrate the system based on the capacitance measurement of the reference capacitor; and
c.) reconstruct a three-dimensional volume-image from the input data collected by the data acquisition electronics;
a balance signal line electrically connected to the output of the three-dimensional sensor for providing a balance signal to the system to mitigate the effect of drift; and
a receiver amplifier having an input and output, wherein the input of the receiver amplifier is electrically connected with the output of the three-dimensional sensor and wherein the output of the receiver amplifier is in electrical communication with the data acquisition electronics.

21. A system for generating a three-dimensional tomograph of a vessel interior or other object, the system comprising:
a three-dimensional capacitance sensor device comprising a plurality of electrodes for placement around the vessel or the object, wherein the three-dimensional capacitance sensor device is adapted to provide electric field distribution and sensor sensitivity in three geometric dimensions, wherein the three-dimensional capacitance sensor has an input and an output;
data acquisition electronics in communication with the output of the three-dimensional capacitance sensor device for receiving input data from the three-dimensional capacitance sensor device; and
a processing system in communication with the data acquisition electronics, the processing system programmed with instructions for executing on the processing system to reconstruct a three-dimensional volume-image from the input data collected by the data acquisition electronics;
wherein the three-dimensional capacitance sensor device is an adaptive electrical capacitance volume tomography sensor device and wherein the plurality of electrodes are each comprised of a plurality of capacitance segments;

wherein the plurality of capacitance segments of at least one electrode are individually addressable with voltages, the system further comprising:

a tunable band pass filter in electrical communication with the output of the three-dimensional capacitance sensor device;

a reference capacitor of a fixed predetermined value electrically connected to the input of the three-dimensional capacitance sensor device and wherein the data acquisition electronics is in electrical communication with the reference capacitor for obtaining the capacitance measurement of the reference capacitor;

wherein the processing system is programmed with instructions for executing on the processing system to:
  a.) use the capacitance measurement of the reference capacitor as a reference for calibration of the system; and
  b.) calibrate the system based on the capacitance measurement of the reference capacitor and use the capacitance measurement of the reference capacitor to back calculate capacitance values or to set calibration parameters for the three-dimensional capacitance sensor device; and wherein the processing system is programmed with instructions for executing on the processing system to identify a location of active electricity within the three-dimensional capacitance sensor device.

* * * * *